(12) United States Patent
Kaneko et al.

(10) Patent No.: US 11,517,219 B2
(45) Date of Patent: Dec. 6, 2022

(54) BIOLOGICAL INFORMATION MEASUREMENT APPARATUS

(71) Applicant: CANON KABUSHIKI KAISHA, Tokyo (JP)

(72) Inventors: Daisuke Kaneko, Suntou-gun (JP); Motohiro Furusawa, Shizuoka (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 925 days.

(21) Appl. No.: 16/364,298

(22) Filed: Mar. 26, 2019

(65) Prior Publication Data

US 2019/0298225 A1   Oct. 3, 2019

(30) Foreign Application Priority Data

Mar. 27, 2018   (JP) .............................. JP2018-060733

(51) Int. Cl.
*G01N 21/27*     (2006.01)
*A61B 5/103*     (2006.01)
(Continued)

(52) U.S. Cl.
CPC .......... *A61B 5/1032* (2013.01); *A61B 5/0075* (2013.01); *A61B 5/02108* (2013.01);
(Continued)

(58) Field of Classification Search
CPC .... G01N 21/274; G01N 21/251; G01N 21/25; A61B 5/0075; A61B 5/6826
See application file for complete search history.

(56) References Cited

U.S. PATENT DOCUMENTS 9,066,052 B2   6/2015   Takemura
9,808,162 B2   11/2017  Uedaira et al.
(Continued)

FOREIGN PATENT DOCUMENTS

CN   101848673 A   9/2010
CN   103619239 A   3/2014
(Continued)

OTHER PUBLICATIONS

U.S. Appl. No. 16/364,313, Toshifumi Kitamura, filed Mar. 26, 2019.
(Continued)

*Primary Examiner* — Maurice C Smith
(74) *Attorney, Agent, or Firm* — Venable LLP

(57) ABSTRACT

A biological information measurement apparatus comprises: a spectrometer; a housing that contains the spectrometer and includes a surface on which a measurement target is to be placed, and an aperture portion through which light illuminating the measurement target placed on the surface and light reflected from the measurement target are to pass; and a shutter member that can move between a first position of opposing the aperture portion of the housing and a second position of retreating from the first position of opposing the aperture portion, the shutter member including a white reference surface. If the shutter member is at the first position, the spectrometer performs calibration using the white reference surface. If the shutter member is at the second position, the aperture portion and the measurement target oppose each other, and the spectrometer colorimetrically measures the measurement target.

14 Claims, 9 Drawing Sheets

(51) Int. Cl.
*A61B 5/00* (2006.01)
*A61B 5/021* (2006.01)
*B08B 1/00* (2006.01)

(52) U.S. Cl.
CPC ............ *A61B 5/6843* (2013.01); *B08B 1/002* (2013.01); *B08B 1/005* (2013.01); *G01N 21/27* (2013.01); *G01N 21/274* (2013.01); *A61B 2560/0223* (2013.01)

(56) References Cited

U.S. PATENT DOCUMENTS

| | | |
|---|---|---|
| 2006/0062437 A1 | 3/2006 | O'Gorman |
| 2009/0124853 A1 | 5/2009 | Gono |
| 2010/0141380 A1 | 6/2010 | Pishva |
| 2014/0081093 A1 | 3/2014 | Kim |
| 2015/0157247 A1 | 6/2015 | Weinstein |
| 2018/0199831 A1 | 7/2018 | Kawachi |

FOREIGN PATENT DOCUMENTS

| | | | |
|---|---|---|---|
| CN | 107708536 A | 2/2018 | |
| DE | 202009008707 U1 * | 12/2010 | ............ G01J 1/0204 |
| JP | 4-88586 A | 3/1992 | |
| JP | 2004-000467 | 1/2004 | |
| JP | 2006-000181 | 1/2006 | |
| JP | 2007-229164 A | 9/2007 | |
| JP | 2010-530555 A | 9/2010 | |
| JP | 2011022114 A * | 2/2011 | |
| JP | 2013-225324 A | 10/2013 | |
| JP | 2014-131206 | 7/2014 | |
| JP | 2016-083030 | 5/2016 | |
| WO | 2008/139631 A1 | 11/2008 | |
| WO | 2015/046429 A1 | 4/2015 | |

OTHER PUBLICATIONS

U.S. Appl. No. 16/364,261, Hitoshi Furukawa, filed Mar. 26, 2019.
U.S. Appl. No. 16/364,255, Norio Matsui, filed Mar. 26, 2019.

* cited by examiner

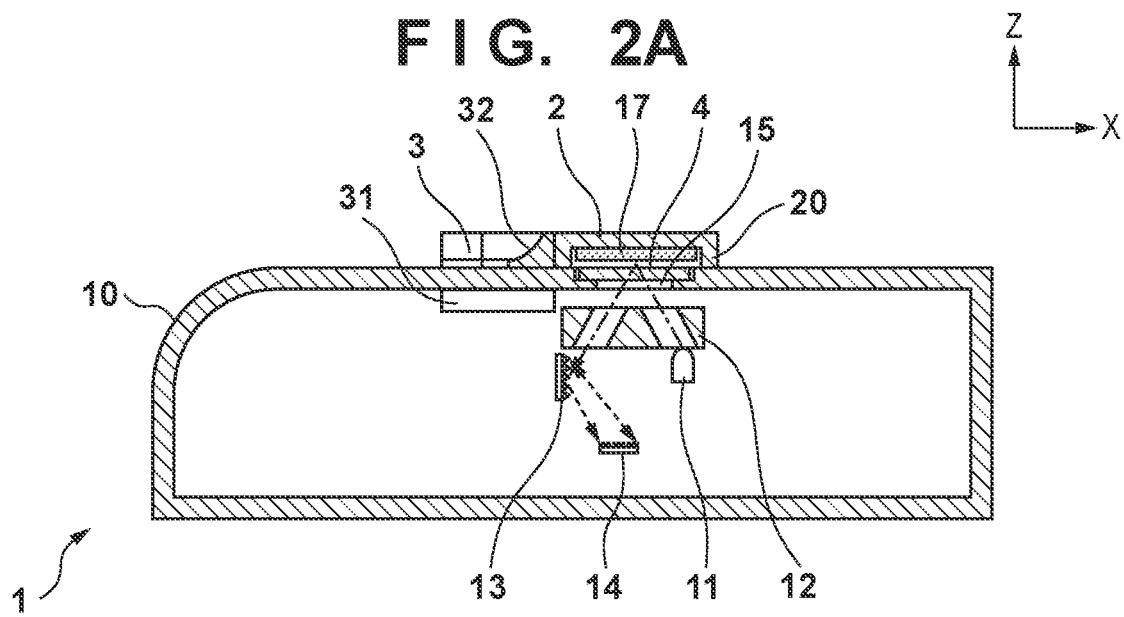
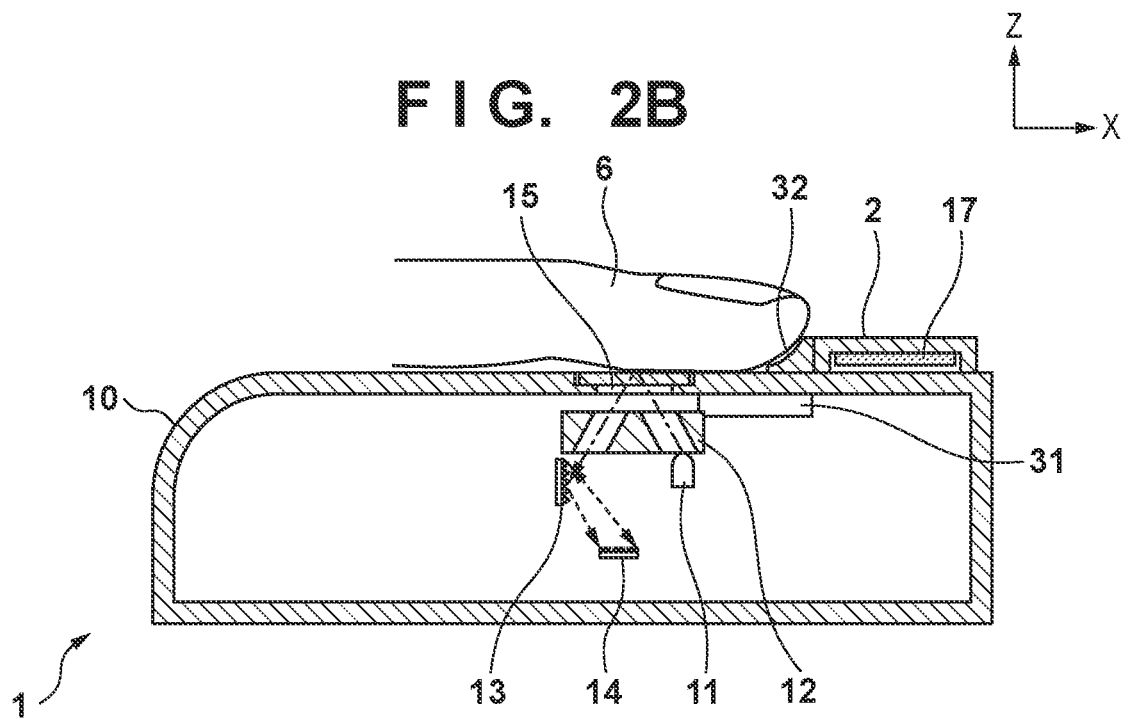

BIOLOGICAL INFORMATION MEASUREMENT APPARATUS

BACKGROUND OF THE INVENTION

Field of the Invention

The present invention relates to a biological information measurement apparatus for measuring biological information by illuminating a living body with light and detecting temporal variation in the light amount of the reflected light or transmitted light therefrom.

Description of the Related Art

In recent years, a vital sensor has been commercially available which illuminates part of a human body with light having a specific wavelength and detects a blood pulse wave (hereinafter referred to as a pulse wave) accompanying the movement of blood by using a light receiving sensor to detect the amount of reflected light or the amount of transmitted light from blood moving through blood vessels in a living body. In general, this type of vital sensor detects the pulse wave by illuminating a target region with light using an LED having a predetermined wavelength as a light source, detecting the amount of light that was reflected from or has passed through the target region using a light receiving sensor, and measuring the amount of variation in the output over time. An LED light source having a green wavelength or a red wavelength, for example, is used as the LED having the predetermined wavelength. Japanese Patent Laid-Open No. 2004-000467 discloses a pulse wave measuring apparatus that illuminates a fingertip portion with a luminous flux emitted from a light source, receives the reflected light therefrom with a photoelectric conversion light receiving sensor, and measures and evaluates the temporal variation in the amount of received light.

In the light emitted from the LED being used as the above-described light source, light of the predetermined wavelength is dominant, but light of other wavelengths is included, which causes noise due to the light of the unneeded wavelength components. Also, due to light rays from the outside entering the light receiving sensor in combination with the reflected or transmitted light from the target portion, unneeded wavelength components have been added to the light reception signal as noise. Although there is no problem with simple processing involving obtaining the pulse rate based on the waveform of the variation (i.e., the pulse wave) in the amount of received light, the influence of the light of the other wavelengths appears when performing a calculation such as finding the differential of the waveform.

A spectrometer is given as a configuration for accurately obtaining the light amount of light of a specific frequency. Japanese Patent Laid-Open No. 2014-131206 discloses a spectrometer as a means for preparing a white light source and obtaining a desired wavelength from the reflected light of the light illuminating from the light source. It is thought that by using this kind of spectrometer as a vital sensor, it is possible to more accurately measure the light amount at a specific wavelength.

The spectrometer requires calibration for preventing a reduction in measurement accuracy caused by factors such as variation in the output of the light source due to the ambient temperature. With the calibration, a correction value for correcting the measurement value is obtained by measuring the reflected light from a white reference plate arranged at a position opposing the spectrometer. The white reference plate needs to retreat to a position that does not hinder measurement when the measurement target is to be measured. When an attempt is made to automatically implement this kind of retreat of the white reference plate, a configuration such as a sensor that captures spatial position information of the measurement target or an actuator with good responsiveness is needed, which leads to increased complexity, size, and cost of the apparatus. On the other hand, allowing a user to implement an operation of arranging the white reference plate at the position opposing the spectrometer for calibration and causing the white reference plate to retreat for pulse wave measurement each time pulse wave measurement is to be performed impairs the ease of measurement.

SUMMARY OF THE INVENTION

The present invention provides a biological information measurement apparatus that is equipped with a spectrometer and has good usability.

According to one aspect of the present invention, there is provided a biological information measurement apparatus, comprising: a spectrometer; a housing that contains the spectrometer and includes a surface on which a measurement target is to be placed, and an aperture portion through which light illuminating the measurement target placed on the surface and light reflected from the measurement target are to pass; and a shutter member that can move between a first position of opposing the aperture portion of the housing and a second position of retreating from the first position of opposing the aperture portion, the shutter member including a white reference surface, wherein if the shutter member is at the first position, the spectrometer performs calibration using the white reference surface, and if the shutter member is at the second position, the aperture portion and the measurement target oppose each other, and the spectrometer colorimetrically measures the measurement target.

Further features of the present invention will become apparent from the following description of exemplary embodiments with reference to the attached drawings.

BRIEF DESCRIPTION OF THE DRAWINGS

FIGS. 2A and 2B are schematic cross-sectional views showing the pulse wave measuring apparatus according to the first embodiment.

DESCRIPTION OF THE EMBODIMENTS

Hereinafter, embodiments of the present invention will be described with reference to the accompanying drawings.

First Embodiment

The following describes a small-size biological information measurement apparatus that uses a spectrometer to stably detect, with high accuracy, components such as a pulse wave caused by pulsation accompanying blood in a human body moving through blood vessels accompanying a heartbeat, and the amount of oxygen in the blood. It should be noted that the measurement target of the biological information in the first embodiment is a finger of a user, and the biological information to be measured is a pulse wave. A configuration of a pulse wave measuring apparatus 1 serving as a biological information measurement apparatus according to a first embodiment will be described with reference to FIGS. 1A to 1C and 2A to 2D.

Figure 1A:
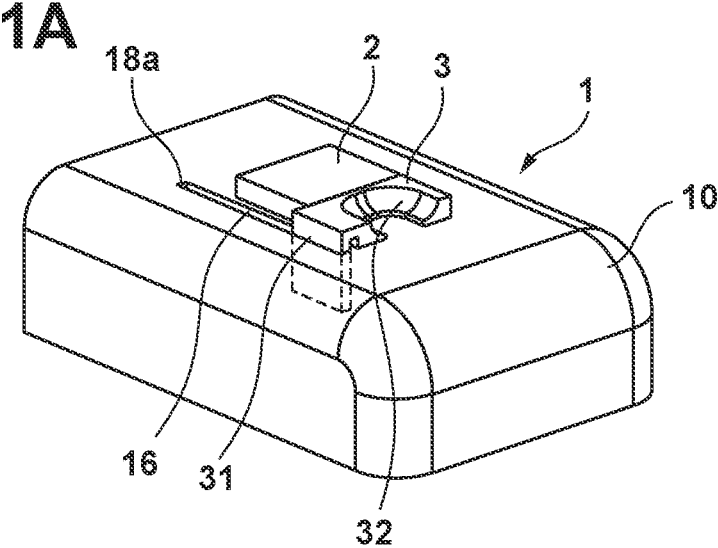
FIGS. 1A to 1C are external perspective views showing a pulse wave measuring apparatus according to a first embodiment.
Figure 1B:
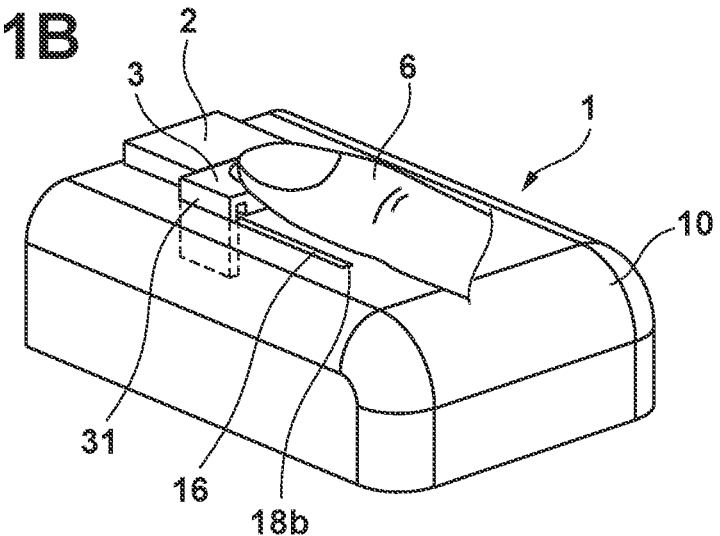
Figure 1C:
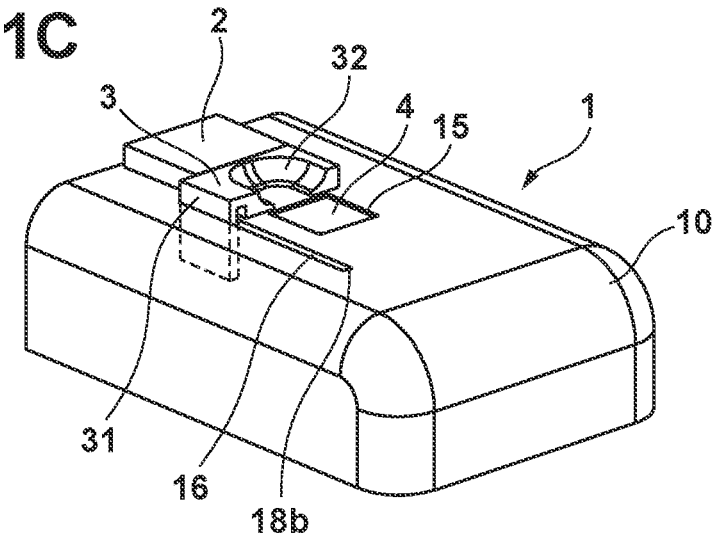

FIGS. 1A to 1C are external perspective views showing the pulse wave measuring apparatus 1. The pulse wave measuring apparatus 1 has a housing 10 that contains a spectrometer. The upper surface of the housing 10 is a surface on which the measurement target is to be placed. The upper surface of the housing 10 is provided with an aperture portion 15 that enables the coming and going of light between a measurement target placed on the upper surface and the spectrometer inside of the housing 10, and a transparent cover 4 composed of a transparent material that covers the aperture portion 15. That is, the light illuminating the measurement target placed on the upper surface of the housing 10 and the light reflected from the measurement target pass through the aperture portion 15. Also, the upper portion of the aperture portion 15 and the transparent cover 4 is provided with a shutter member 2, and a guide member 3 for guiding the measurement target. It should be noted that FIG. 1A shows a state in which the shutter member 2 covers the aperture portion 15, FIG. 1B shows a state in which the shutter member 2 has retreated, the aperture portion 15 is open, and a finger 6, which is the measurement target, covers the opening portion 15, and FIG. 1C is a diagram in which the illustration of the finger is omitted in the state shown in FIG. 1B.

In the present embodiment, the shutter member 2 and the guide member 3 are connected, or are constituted integrally. The guide member 3 has a guide shape portion 31 and a finger receiving portion 32. The guide member 3 and the shutter member 2 can perform a sliding movement in the X direction shown in FIGS. 1A to 1C due to the guide shape portion 31 and a guide rail portion 16 provided on the housing 10. The two end portions of the guide rail portion 16 function as a stopper portion 18a and a stopper portion 18b, and define two positions, namely a position at which the guide shape portion 31 abuts against the stopper portion 18a, and a position at which the guide shape portion 31 abuts against the stopper portion 18b. Accordingly, due to the guide member 3 being moved by the finger 6, the shutter member 2 can move between a first position (FIG. 1A) opposing the aperture portion 15 of the housing 10, and a second position (FIG. 1C) of having retreated from the first position of opposing the aperture portion 15. That is, the shutter member 2 receives the force of moving from the first position to the second position due to the measurement target being located at the aperture portion 15.

FIGS. 2A and 2B are schematic cross-sectional views of the pulse wave measuring apparatus 1 viewed from the Y direction shown in FIGS. 1A to 1C. FIG. 2A shows a state in which the aperture portion 15 is covered by the shutter member 2, and FIG. 2B shows a state in which the shutter member has retreated from the aperture portion 15 due to the finger 6 serving as the measurement target being placed thereon.

Figure 2C:
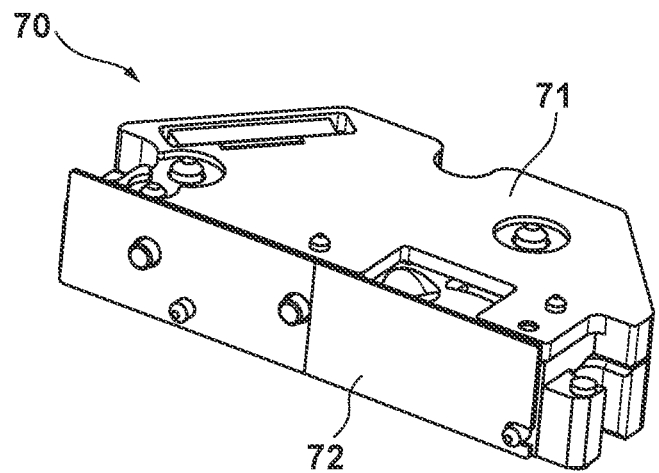
FIGS. 2C and 2D are diagrams showing an example of a structure of a spectrometer to be used in the pulse wave measuring apparatus.

A spectrometer (to be described later with reference to FIGS. 2C and 2D) that colorimetrically measures the measurement target is contained in the housing 10, and the optical system thereof is shown schematically in FIGS. 2A and 2B. As shown in FIGS. 2A and 2B, the optical system of the spectrometer includes: a white LED 11, which is a light-emitting source for illuminating the measurement target; a light guide 12; a diffraction grating 13; and a line sensor 14. The light from the white LED 11 is guided to the aperture portion 15 by the light guide 12, passes through the aperture portion 15, and illuminates the measurement target. The reflected light from the measurement target is guided to the diffraction grating 13 by the light guide 12. The reflected light is dispersed into respective wavelengths by the diffraction grating 13, and the line sensor 14 receives the dispersed light.

Figure 2D:
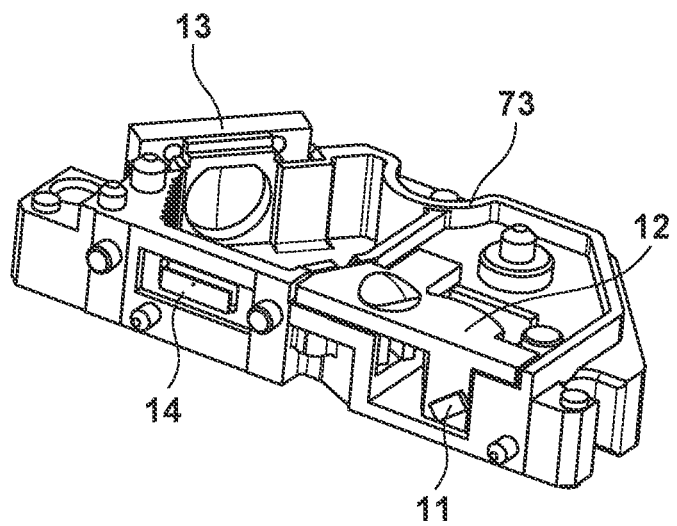

FIGS. 2C and 2D are diagrams showing a structure of a spectrometer 70 contained in the housing 10 of the pulse wave measuring apparatus 1. FIG. 2C shows the external appearance of the spectrometer 70. An outer shell of the spectrometer 70 is formed by a cover portion 71 and a case portion 73. An electric substrate 72 has a circuit for amplifying the signal from the line sensor 14, performing A/D conversion on the resulting signal, and thus obtaining an output signal (digital signal) for each wavelength. FIG. 2D shows a state in which the electric substrate 72 and the cover portion 71 have been removed from the spectrometer 70 shown in FIG. 2C. The spectrometer 70 includes an integrated structure in which the optical system including the above-described white LED 11, light guide 12, diffraction grating 13, and line sensor 14 are incorporated in the case portion 73, and thus a smaller size is realized.

As shown in FIGS. 1A to 1C and FIGS. 2A to 2B, the housing 10 is provided with the transparent cover 4 so as to cover the aperture portion 15 in order to prevent a reduction of the measurement accuracy caused by foreign matter falling into the optical system of the internal spectrometer. The transparent cover 4 also serves the purpose of preventing a soft measurement target such as a finger from deforming and entering the interior of the housing 10 when the measurement target is placed on the aperture portion 15, keeping the distance between the optical system of the spectrometer and the measurement target constant, and stabilizing the measurement environment. A white reference member 17 used for calibration of the spectrometer 70 is fixed to the shutter member 2 on the surface of the shutter member opposing the aperture portion 15 in FIG. 2A. It should be noted that the white reference member 17 has a white reference surface that is arranged so as to reflect the light from the spectrometer 70, and the area of the white reference surface is larger than the area of the aperture portion 15.

Next, a procedure performed when using the pulse wave measuring apparatus 1 to measure a pulse wave, and an operation of the pulse wave measuring apparatus 1 will be described with reference to FIGS. 1A to 1C and FIGS. 2A and 2B.

In a pulse wave non-measurement mode in which the pulse wave is not measured, the pulse wave measuring apparatus 1 waits in the state shown in FIGS. 1A and 2A. In this standby state, the white reference member 17 is located at a position opposing the aperture portion 15, that is, the position opposing the spectrometer 70, and the spectrometer 70 can implement calibration. "Calibration" in the present embodiment refers to calculating a correction value by sensing a white reference member with respect to irregularity in the light amount of the light source and variation in the sensitivity of the sensor or the like, and thus correcting the output of the wavelengths.

Then, when the pulse wave is to be measured, the user brings the tip of the finger 6 to be measured into contact with the finger receiving portion 32 of the guide member 3 in the X direction and slides the guide member 3 in the X direction. The guide rail portion 16 has a stopper portion 18*a*, and the pulse wave measuring apparatus 1 enters a state in which measurement of the pulse wave can be implemented (hereinafter referred to as "pulse wave measurement mode") at the position at which the guide shape portion 31 that was slid abuts against the stopper portion 18*a*. In the pulse wave measurement mode, the positional relationship between the measurement target and the aperture portion 15 is approximately constant due to the finger receiving portion 32 of the guide member 3 reaching the stopper portion 18*a*. For this reason, in the pulse wave measuring apparatus 1, if the same finger is set as the measurement target, the pulse wave in the same region can be stably measured and the reproducibility of the measurement environment can be increased.

Also, the movements of the guide member 3 and the shutter member 2 are linked. For this reason, when the user moves the finger 6 to the measured position in accordance with the guiding of the guide member 3, the white reference member 17 for calibration retreats from the position of opposing the aperture portion 15. As a result, the user no longer needs to be aware of the sequence by which the white reference member 17 retreats from the aperture portion 15, and operability improves. Furthermore, since the retreat of the white reference member 17 is realized by the operation performed by the user, the pulse wave measuring apparatus 1 can realize a retreating function of the white reference member 17 with a simple configuration.

Figure 3A:
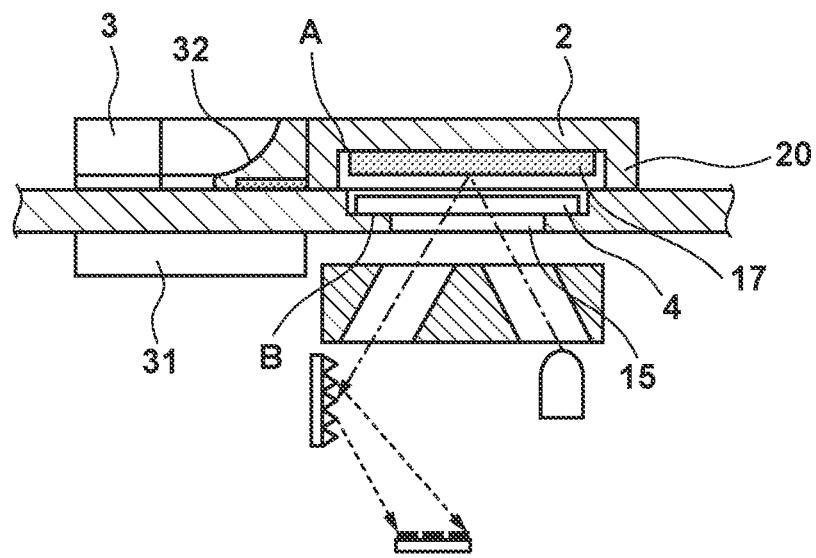
FIGS. 3A and 3B are schematic cross-sectional views showing the vicinity of an aperture portion of the pulse wave measuring apparatus according to the first embodiment.

Also, the shutter member 2 of the present embodiment includes a wall-shaped portion (hereinafter referred to as a wall portion 20) so as to surround the white reference member 17. FIG. 3A is an enlarged view of the vicinity of the aperture portion 15 shown in FIG. 2A. As shown in FIG. 3A, the end surface of the wall portion 20 comes into contact with the upper surface of the housing 10. That is, the end surface of the wall portion 20 provided so as to surround the white reference member 17 comes into contact with the periphery of the aperture portion 15 and the transparent cover 4 on the upper surface of the housing 10. Accordingly, the light emitted by the white LED 11 is prevented from leaking to the outside in the pulse wave non-measurement mode. Note that the wall portion 20 is not essential. For example, it is also possible to use a configuration in which the entirety of the lower surface of the shutter member 2 is used as the white reference surface and no wall portion 20 is provided. In this case, the lower surface opposing the aperture portion 15 of the shutter member 2 abuts against at least the upper surface of the periphery of the transparent cover 4 in the housing 10.

Then, when the shutter member 2 is to retreat for the pulse wave measurement, the user slides the shutter member 2 via the guide member 3 with the finger 6, and the finger 6 traces over the path of the shutter member 2. According to this configuration, in the period from calibration to the pulse wave measurement mode, the aperture portion 15 is always in a state of being closed by the shutter member 2 or by the finger 6 of the user. For this reason, it is possible to prevent the user from directly viewing the visible light of the white LED 11 that blinks during calibration and measurement of the pulse wave, and from feeling that the visible light is bright.

Also, as shown in FIG. 3A, the upper surface of the transparent cover 4 is provided so as to be at a position that is the same height as or lower than the upper surface of the housing 10. This is a configuration for preventing the wall portion 20 from catching on the end portion of the transparent cover 4 and hindering the sliding movement of the shutter member 2 when sliding the shutter member 2. Note that the shadow-casting region of the shutter member 2 on the upper surface of the housing 10 is of such a size that it covers at least the entirety of the transparent cover 4 when the shutter member 2 is at the first position (the position at the stopper portion 18*b* side). More preferably, the area A of the region surrounded by the wall portion 20 of the shutter member 2 is greater than or equal to the sum of the area B of the region of the housing that provides the region for fixing the transparent cover 4 and the area of the aperture portion. Accordingly, the end surface of the wall portion 20 and the upper surface of the housing 10 can be brought into contact with each other so as to prevent external light from reaching the sensor while the shutter member 2 is at the first position for calibration.

It should be noted that in the present embodiment, the shutter member 2 and the white reference member 17 are constituted by different members, but there is no limitation to this. If the surface opposing the aperture portion inside of the shutter member 2 is constituted by the same white color as the white reference member 17, the shutter member 2 can satisfy the function of the white reference member and the above-described effect can be obtained.

On the other hand, it is desirable that the inner circumferential surface of the wall portion 20 is black. This is for preventing the light obtained by the light from the white LED 11 being reflected diffusely and scattered by the white reference member 17 from being reflected on the inner circumferential surface of the wall portion 20 during calibration. Accordingly, the influence that the diffusely reflected light reaching the sensor has on the calibration is reduced. It should be noted that there is no limitation to the case in which the area A is sufficiently larger than the sum of the area B and the area of the aperture portion such that the diffusely reflected light that occurs due to the wall shape does not influence the output of the sensor. Also, there is no limitation to the case in which the reflection surface of the light of the white reference member 17 is sufficiently near the measurement surface (the upper surface of the housing 10).

Figure 3B:
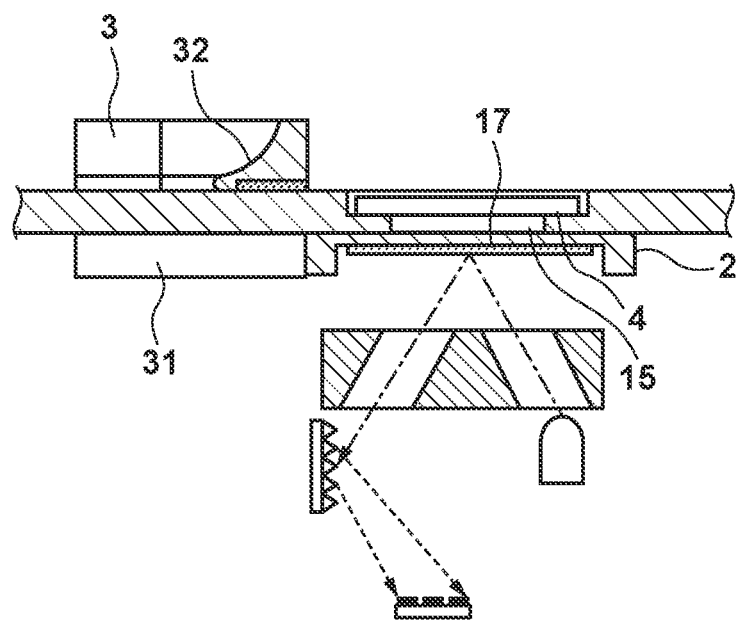

It should be noted that the above description indicated a configuration in which the shutter member 2 is arranged outside of the housing 10, but there is no limitation to this, and as shown in FIG. 3B, the shutter member 2 may also be arranged inside of the housing 10. In FIG. 3B, the shutter member 2 is connected to the guide shape portion 31 of the guide member 3 in the interior of the housing 10. The shutter member 2 and the white reference member 17 moves to the retreat position due to the shutter member 2 moving accompanying the movement of the guide member 3.

MODIFIED EXAMPLE

Figure 4A:
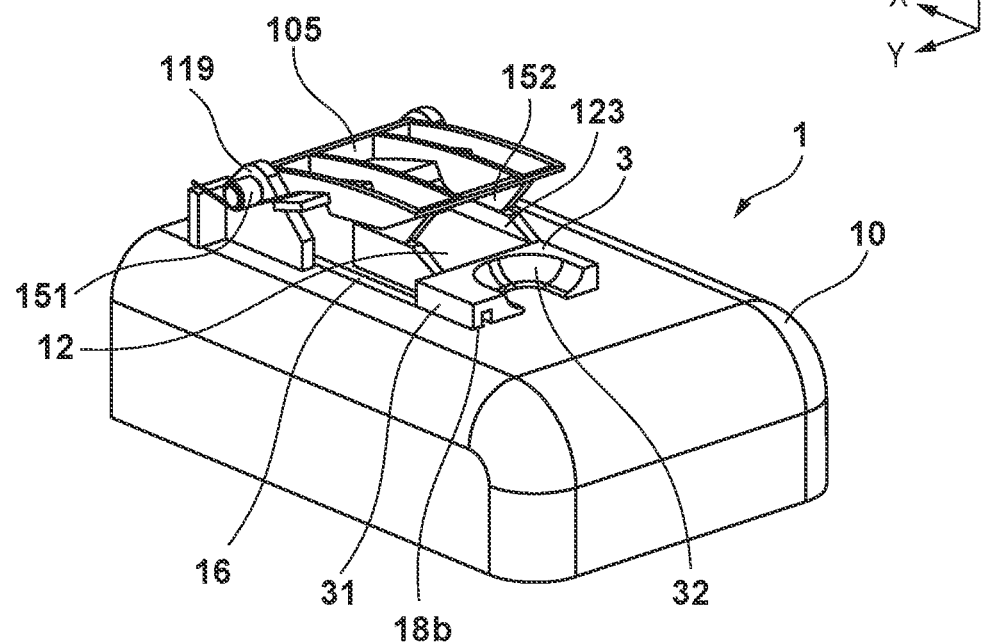
FIGS. 4A and 4B are external perspective views showing a pulse wave measuring apparatus according to a modified example.
Figure 4B:
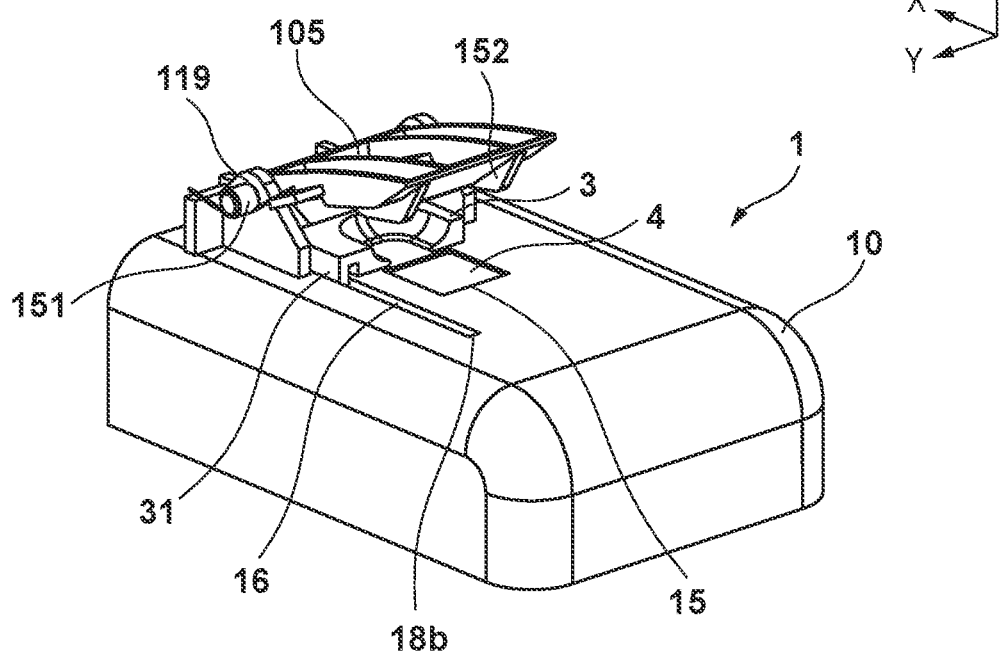
Figure 5A:
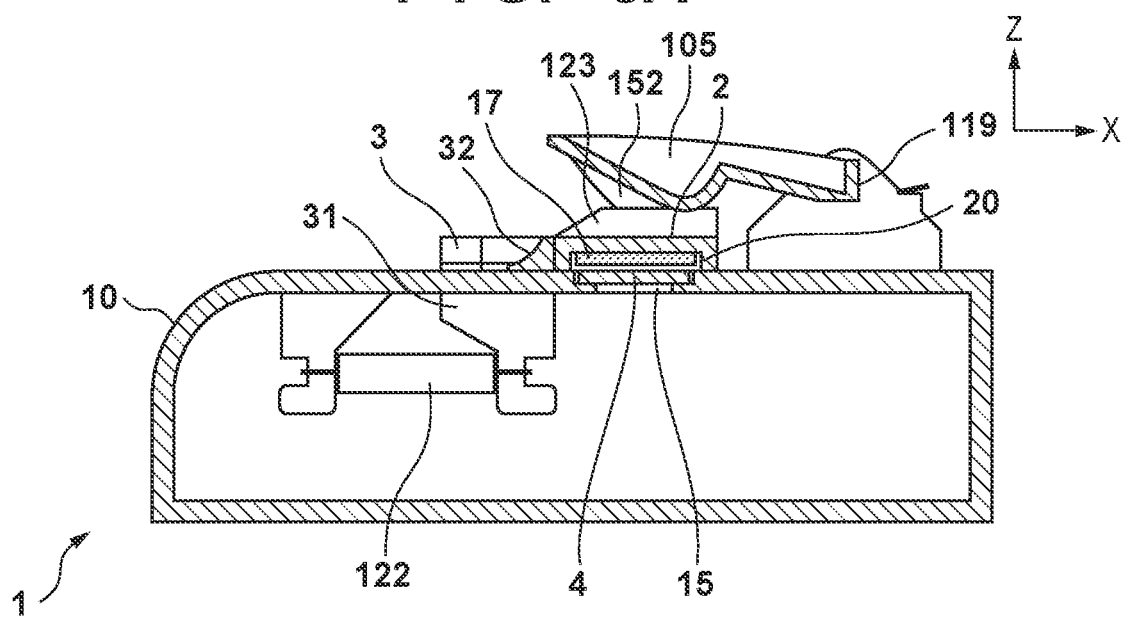
FIGS. 5A and 5B are schematic cross-sectional views showing the pulse wave measuring apparatus according to the modified example.
Figure 5B:
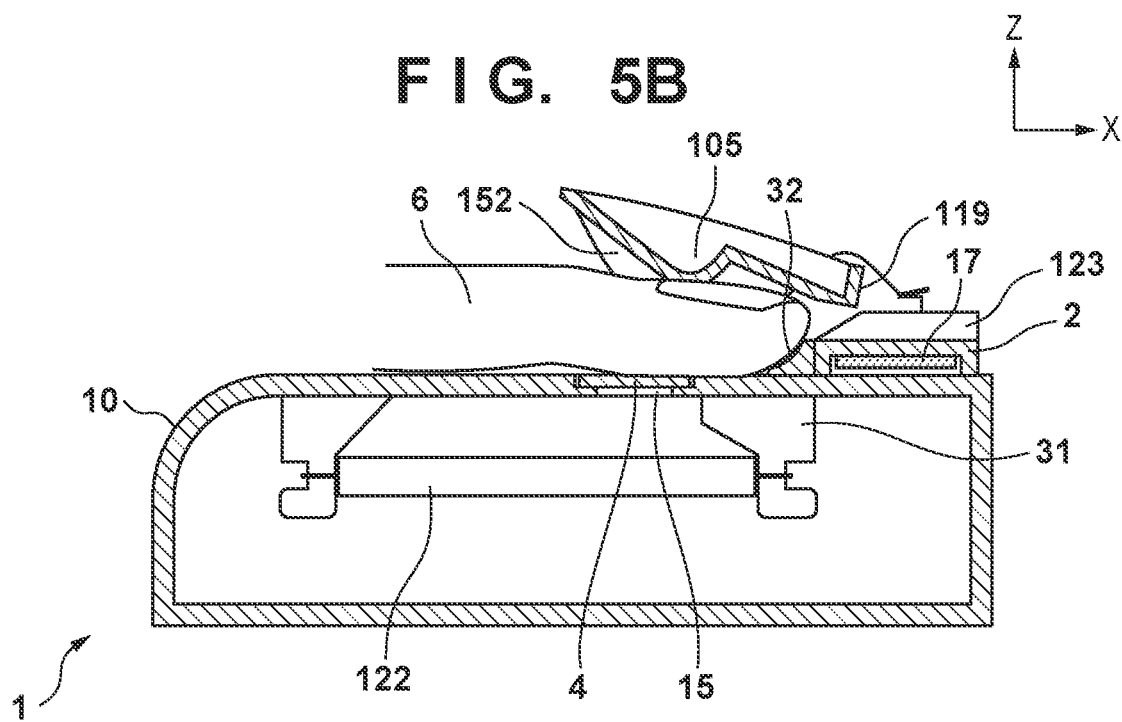

In the first embodiment described with reference to FIGS. 1A to 1C, FIGS. 2A to 2D, and FIGS. 3A and 3B, a configuration of the lowest level required to solve the above-described problem was described, but a secondary effect such as further improving the measurement accuracy can be obtained by adding the configurations described hereinafter. The configuration of this modified example will be described with reference to FIGS. 4A and 4B and FIGS. 5A and 5B. FIGS. 4A and 4B are external perspective views of the pulse wave measuring apparatus 1 according to the modified example, and FIGS. 5A and 5B are schematic cross-sectional views from the Y direction shown in FIGS. 4A and 4B. Note that in FIGS. 4A and 4B and FIGS. 5A and 5B, configurations having similar functions to those of the first embodiment (FIGS. 1A to 1C, FIGS. 2A to 2D, and FIGS. 3A and 3B) are denoted by identical reference numerals.

Similarly to the first embodiment, the pulse wave measuring apparatus 1 according to the modified example includes: a housing 10; an aperture portion 15 on the upper surface of the housing 10; a transparent cover 4 that covers the aperture portion 15; a shutter member 2; and a guide member 3 that guides the measurement target. Also, the pulse wave measuring apparatus 1 according to the modified example includes a press member 105 and a press spring 151 for causing the measurement target to be in close contact with the transparent cover 4 in the pulse wave measurement mode. The press member 105 is pivotably held by a bearing portion 119 provided on the housing 10.

FIGS. 4A and 5A show a state in which the shutter member 2 is at the first position and covers the aperture portion 15 (pulse wave non-measurement mode). FIGS. 4B and 5B show a state in which the shutter member 2 has retreated and is at the second position, the aperture portion 15 is open, and a finger 6 has been placed thereon (pulse wave measurement mode). It should be noted that in FIG. 4B, similarly to FIG. 1C, the finger 6 serving as the measurement target placed on the upper surface of the housing 10 is not illustrated. Also, in FIGS. 5A and 5B, the configuration of the optical system of the spectrometer 70 (white LED 11, light guide 12, diffraction grating 13, line sensor 14) is not illustrated.

The pulse wave measuring apparatus 1 according to the modified example has a configuration similar to that of the first embodiment described with reference to FIGS. 1A to 1C and FIGS. 2A to 2D, and therefore it is possible to obtain actions and effects similar to those of the first embodiment. In addition, according to the configuration of the modified example, the effects indicated hereinafter, which lead to pulse wave measurement in a more highly-reproducible measurement environment, can be obtained.

Similarly to the configuration shown in FIGS. 2A and 2B, the shutter member 2 includes a wall portion 20 so as to surround a white reference member 17. The press member 105 includes a pressing rib 152 and the shutter member 2 includes a pressed rib 123. The shutter member 2 is biased toward the upper surface of the housing 10 due to the pressing rib 152 coming into contact with the pressed rib 123 when the shutter member 2 is at the position for calibration (the pulse wave non-measurement mode). With this kind of configuration, the wall portion 20 and the housing 10 have a higher ability of coming into close contact with each other, the influence of outside light during calibration is further reduced, and the environment during the pulse wave measurement can be set to a more stable state. Note that in the pulse wave measurement mode, the finger 6 of the user comes into contact with the press member 105 and pushes up the press member 105, and therefore the pressing rib 152 and the pressed rib 123 separate from each other.

Also, as shown in FIGS. 5A and 5B, the pulse wave measuring apparatus 1 according to the modified example includes a shutter biasing spring 122 that biases the shutter member 2 constituted integrally with the guide member 3 toward the position at which the shutter member 2 covers the aperture portion 15 (in the -X direction shown in FIGS. 5A and 5B). Also, similarly to the embodiment shown in FIGS. 1A to 1C, the shutter member 2 can perform a sliding motion using the guide shape portion 31 provided on the guide member 3 and the guide rail portion 16. The guide rail portion 16 has a stopper portion 18$b$, and the position at which the guide shape portion 31 abuts against the stopper portion 18$b$ is the position of the shutter member 2 for performing calibration (first position). That is, the shutter biasing spring 122 biases the shutter member 2 from the second position, which is the retreat position, to the first position, which is the position at which calibration is possible.

By including the above-described configuration, the shutter member 2 automatically moves to the position at which calibration is possible outside of the pulse wave measurement mode in which the shutter member 2 is slid opposite to the biasing direction by the finger 6 of the user. For this reason, the user does not need to be aware of the sequence of arranging the white reference member 17 opposite to the aperture portion 15 during calibration and the ease of measurement can be improved.

Figure 6:
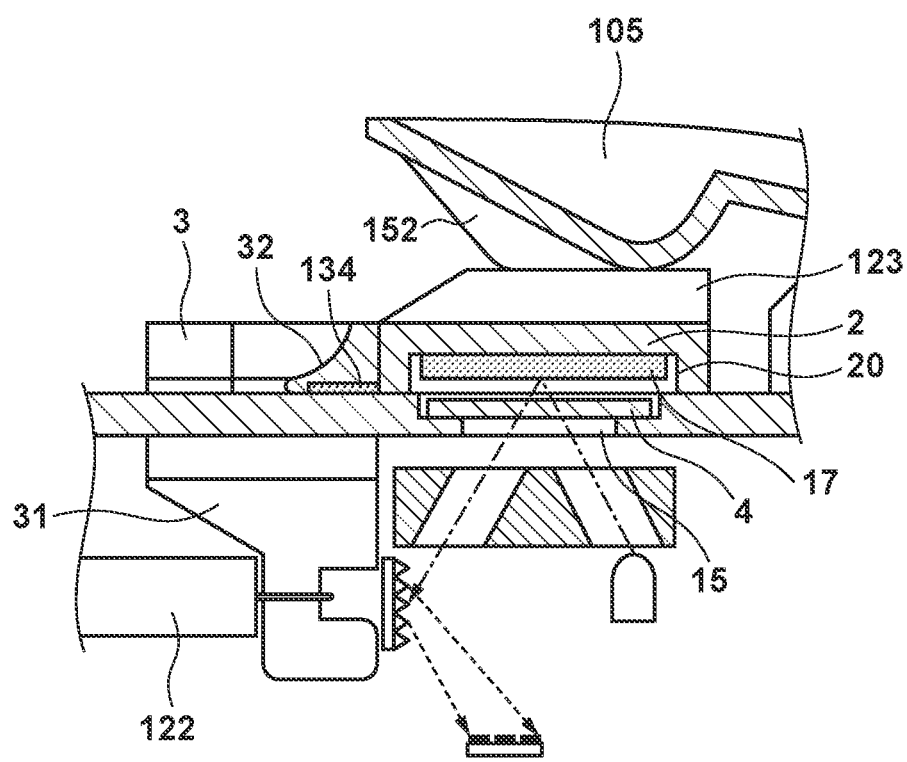
FIG. 6 is a schematic cross-sectional view showing the vicinity of an aperture portion of the pulse wave measuring apparatus according to the modified example.

Furthermore, since the finger 6 of the user comes into contact with the transparent cover 4 each time pulse wave measurement is performed in the above-described first embodiment and the modified example, there is concern that oil on the finger adhering to the transparent cover 4 will influence measurement. In view of this, in the pulse wave measuring apparatus 1 of the modified example, this concern is eliminated due to a cleaning member 134 that comes into contact with the upper surface of the housing 10 or with the transparent cover 4 being integrally provided on the lower portion of the guide member 3. FIG. 6 is a schematic cross-sectional expanded view of the pulse wave measuring apparatus 1 in which the cleaning member 134 is included below the guide member 3. The cleaning member 134 includes an elastic body or deformable material such as rubber or a brush, or includes a bristle-like brush. The cleaning member 134 is compressed by the upper surface of the housing 10 when the guide member 3 is at the position for the pulse wave non-measurement mode, and on the surface of the transparent cover 4, which is located at a higher height, the compression is released and thus the cleaning member 134 can come into contact therewith.

According to the above-described configuration, the cleaning member 134 slides on the surface of the transparent cover 4 each time during a reciprocation in which the guide member 3 is slid upon pulse wave measurement, and thus cleaning is possible. The cleaning is implemented while the guide member 3 guides and moves the finger 6 during pulse wave measurement, and while the guide member 3 and the shutter member 2 are automatically returned to the position for calibration. For this reason, the user no longer needs to perform an independent operation for cleaning the transparent cover 4, and therefore operability improves.

Second Embodiment

Figure 7A:
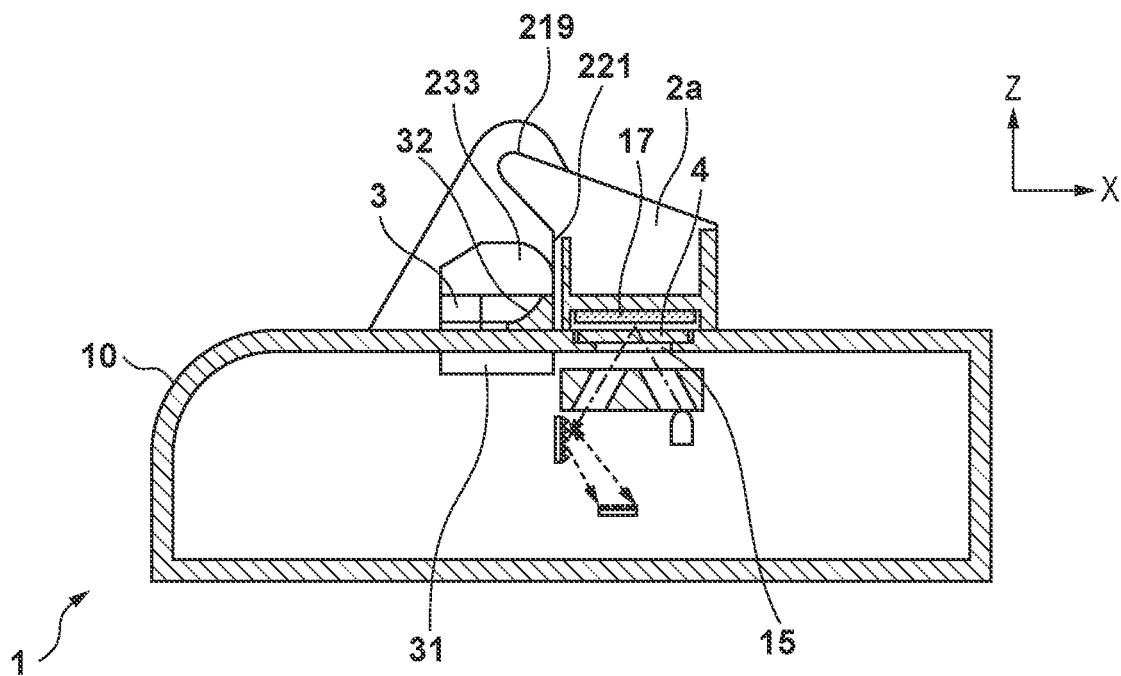
FIGS. 7A and 7B are schematic cross-sectional views showing a pulse wave measuring apparatus according to a second embodiment.
Figure 7B:
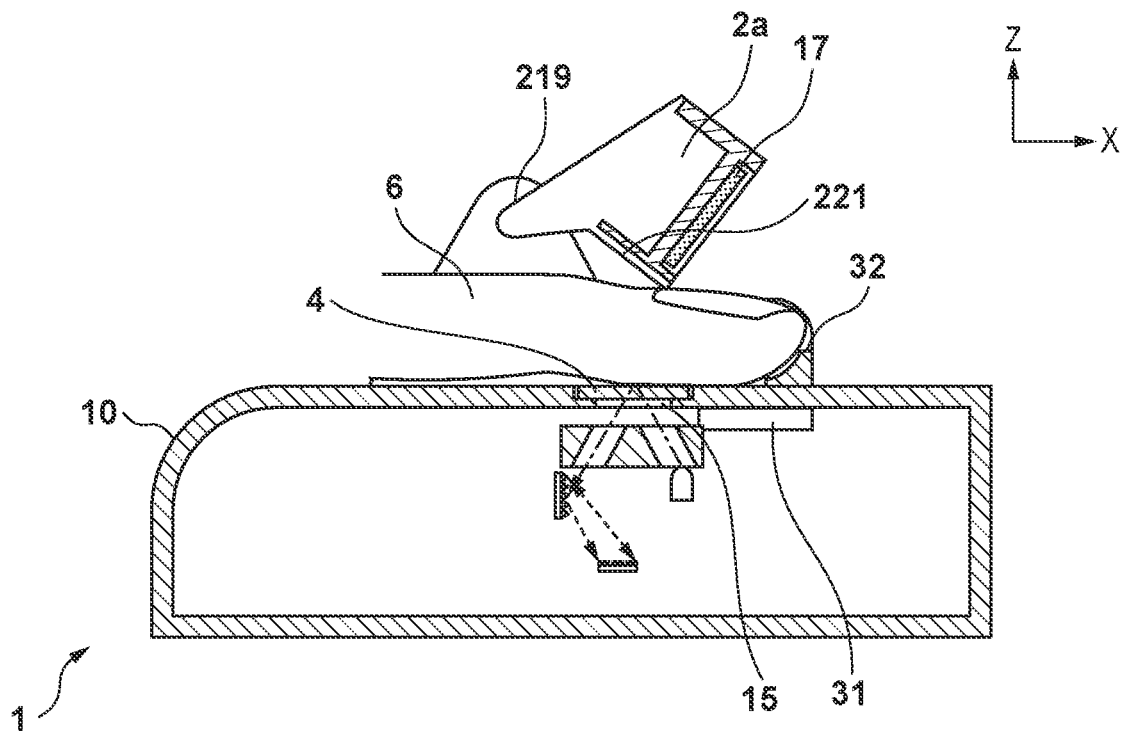

Next, a pulse wave measuring apparatus 1 according to a second embodiment will be described with reference to FIGS. 7A and 7B. FIGS. 7A and 7B are schematic cross-sectional views showing the pulse wave measuring apparatus 1 according to the second embodiment. FIG. 7A shows a state in which a shutter member 2a covers an aperture portion 15, and FIG. 7B shows a state in which the shutter member 2a has retreated, the aperture portion 15 is open, and the finger 6 is placed thereon. It should be noted that configurations having functions similar to those of the first embodiment are denoted by reference numerals that are the same as those of the first embodiment.

Unlike the first embodiment, the second embodiment does not employ a configuration in which the shutter member 2a and the guide member 3 move integrally. As shown in FIGS. 7A and 7B, the pulse wave measuring apparatus 1 according to the second embodiment includes the shutter member 2a and the guide member 3 on the upper portion of a housing 10, which contains a spectrometer. The shutter member 2a is pivotably supported by a bearing portion 219 provided on the housing 10. Accordingly, the shutter member 2a rotates about an axis in a direction (Y direction) that is approximately parallel to the upper surface of the housing 10 and is approximately orthogonal to the X direction. The shutter member 2a can move between the first position (the position for the pulse wave non-measurement mode) and the second position (the position for the pulse wave measurement mode) due to this rotation.

Similarly to the first embodiment, the guide member 3 has a guide shape portion 31 and the finger receiving portion 32, and can perform a sliding movement in the X direction shown in FIGS. 7A and 7B using the guide shape portion 31 and a guide rail portion 16 provided on the housing 10. Also, the guide member 3 includes a cam-shaped portion 233 that comes into contact with a contact-receiving portion 221 provided on the shutter member 2a through the sliding movement in order to cause the shutter member 2a to retreat from the position of opposing the aperture portion 15 (in order to cause the shutter member 2a to move from the first position to the second position).

According to the pulse wave measuring apparatus 1 according to the above-described second embodiment, similarly to the first embodiment, in the pulse wave measurement mode, the positional relationship between the finger receiving portion 32 and the aperture portion 15 at which the measurement target region is to be located is constant, and therefore approximately the same region of the measurement target can be measured. Also, although the guide member 3 and the shutter member 2a are independent members, their movements are linked. Accordingly, while the user moves the finger 6 to the measurement-receiving position due to the guidance of the guide member 3, the shutter member 2a including the white reference member 17 can retreat from the aperture portion 15. For this reason, the user does not need to be aware of the sequence according to which the white reference member 17 retreats. It should be noted that it is clear that it is also possible to provide a configuration for biasing the shutter member 2a from the retreat position (second position) to the position of covering the aperture portion 15 (first position).

Furthermore, according to the configuration of the second embodiment, the following secondary effects are obtained. First, in the second embodiment, the white reference member 17 separates from the upper surface of the housing and is exposed, and therefore it is possible to clean the white reference member 17. Accordingly, it is possible to prevent and reduce abnormalities in calibration, caused by the white reference member 17 becoming dirty due to the attachment of dust or the like.

Also, according to the second embodiment, as shown in FIGS. 7A and 7B, the shutter member 2a, which has retreated due to the cam-shaped portion 233 of the guide member 3, enters a state of being pushed up by the finger 6, which is the measurement target in the pulse wave measurement mode. Accordingly, by providing the shutter member 2a with the biasing force from the second position to the first position, it is possible to apply a biasing force in the direction of coming into close contact with the transparent cover 4 covering the aperture portion 15 to the finger 6. As a result, a function similar to that of the press member 105 shown in the modified example of the first embodiment can be included in the shutter member 2a. It should be noted that, similarly to the above-described modified example, the guide member 3 may also be provided with a member for cleaning the transparent cover 4.

Third Embodiment

Figure 8A:
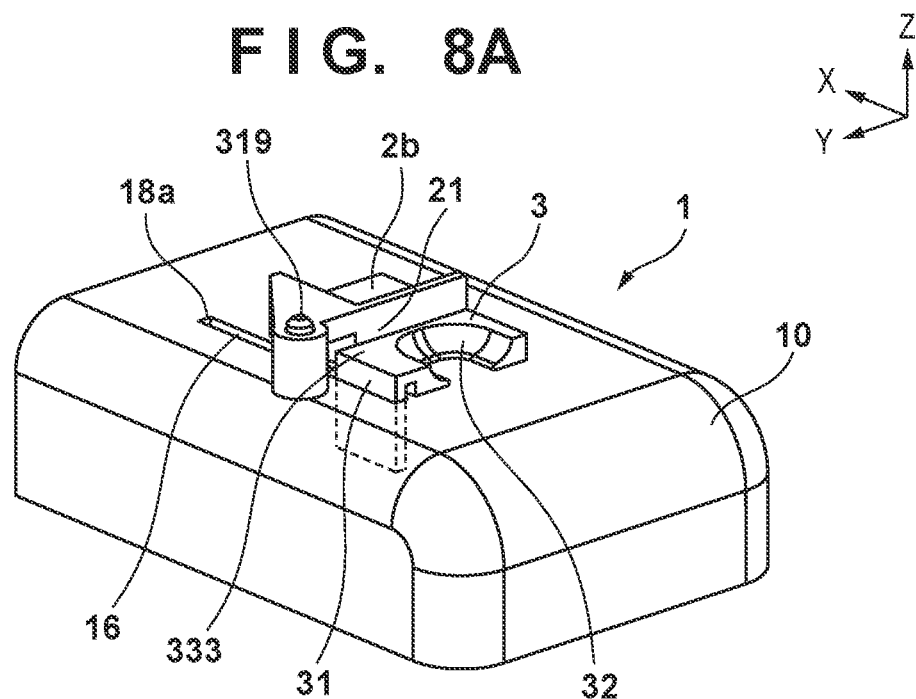
FIGS. 8A and 8B are external perspective views showing a pulse wave measuring apparatus according to a third embodiment.
Figure 8B:
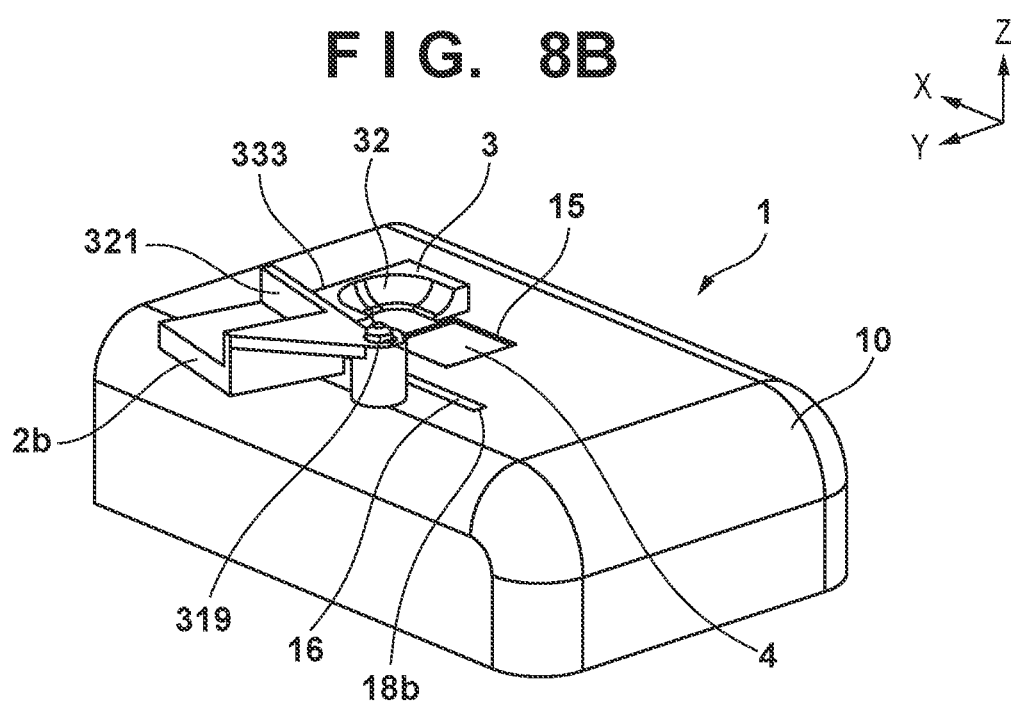

Next, a pulse wave measuring apparatus 1 according to a third embodiment will be described with reference to FIGS. 8A and 8B. FIGS. 8A and 8B are external perspective views showing the pulse wave measuring apparatus 1. FIG. 8A shows a state in which the shutter member 2b covers the aperture portion 15, and FIG. 8B shows a state in which the shutter member 2b has retreated, the aperture portion 15 is open, and the finger 6 has been placed at the measurement position (on the transparent cover 4). It should be noted that in FIG. 8B, the finger 6 is not illustrated. It should be noted that in FIGS. 8A and 8B, configurations having functions similar to those of the first and second embodiments are denoted by the same reference numerals.

In the second embodiment, the shutter member 2a is included as a configuration that can rotate about an axis in a direction parallel to the Y axis. In contrast to this, in the third embodiment, the shutter member 2b is supported so as to be able to pivot about an axis in a direction parallel to the Z axis shown in FIGS. 8A and 8B. That is, in the third embodiment, the shutter member 2b moves between a first position (position of covering the aperture portion 15) and a second position (retreat position) by rotating about an axis that is approximately orthogonal to the upper surface of the housing 10.

As shown in FIGS. 8A and 8B, the pulse wave measuring apparatus 1 according to the third embodiment includes a shutter member 2b and a guide member 3 on an upper portion of the housing 10 of the spectrometer. The shutter member 2b is pivotably supported by a shaft 319 provided on the housing 10. Similarly to the first embodiment, the guide member 3 includes a guide shape portion 31 and a finger receiving portion 32. The guide member 3 can perform a sliding movement in the X direction shown in FIGS. 8A and 8B using the guide shape portion 31 and the guide rail portion 16. Also, the guide member 3 includes a contact shape 333 that comes into contact with a contact-receiving shape portion 321 of the shutter member 2b so as to cause the shutter member 2b to retreat from the position of opposing the aperture portion 15. It should be noted that, similarly to the first embodiment and the second embodiment, it is clear that a configuration for biasing the shutter member 2b from the second position to the first position may also be provided.

The shutter member 2b is configured to be able to retreat from the position of opposing the aperture portion 15 so that the shutter member 2b does not impede the guiding of the measurement target while the measurement target is guided to the aperture portion 15 by the guide member 3. Accordingly, similarly to the first embodiment, the user no longer needs to be aware of the retreat of the shutter member 2b and operability improves. Also, in the pulse wave measurement mode, since the position of the guide member 3 is determined by the stopper portion 18a, the positional relationship between the finger receiving portion 32 and the aperture portion 15 is constant. Accordingly, stability and reproducibility of the measurement environment are provided. It should be noted that, similarly to the above-described modified example, the guide member 3 may also be provided with a member for cleaning the transparent cover 4.

As described above, according to the above-described embodiments, in a pulse wave measuring apparatus that captures temporal variation in the blood flow of a measurement target and daily changes in the pulse waveform, the position of the measurement target can be determined approximately uniquely by the finger receiving portion 32, the guide shape portion 31, and the stopper portion 18. Also, the measurement accuracy is guaranteed since calibration using the white reference member 17 can be executed each time measurement is performed. That is, it is possible to provide a high-accuracy pulse wave measuring apparatus with excellent measurement environment reproducibility. Also, according to the above-described embodiments, the white reference member 17 performs a retreating movement from the position for calibration, accompanying the measurement target being arranged at a position of opposing a spectrometer (measurement position). For this reason, the user can perform pulse wave measurement without being conscious of the arrangement state of the white reference member 17. Furthermore, if a configuration is used in which the white reference member 17 moves to the position of opposing the spectrometer in response to the measurement target being removed from the measurement position, calibration can be executed each time measurement is performed, without the user giving any consideration to the position of the white reference member 17.

As described above, according to the pulse wave measuring apparatus 1 of the above-described embodiments, the user can implement a sequence by which the white reference member 17 retreats without being aware of it by moving the measurement target to the position of the stopper portion 18a in accordance with the guide member 3. Also, approximately the same region of the measurement target can be measured each time. Also, since no configuration for controlling a movable portion such as an actuator is included, the above-described effects can be realized with a simple and low-cost configuration.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-060733, filed Mar. 27, 2018, which is hereby incorporated by reference herein in its entirety.

What is claimed is:

1. A biological information measurement apparatus, comprising:
  a spectrometer contained within a housing;
  the housing including a surface configured to receive a measurement target, and an aperture portion configured to pass light illuminating the measurement target placed on the surface and light reflected from the measurement target;
  a shutter member configured to move between a first position of opposing the aperture portion and a second position of of not opposing the aperture portion, the shutter member including a white reference surface; and
  a guide member arranged on the housing surface that is configured to come into contact with the measurement target and guide the measurement target to the aperture portion, wherein
  the shutter member is moved by the measurement target from the first position to the second position,
  the guide member moves in a first direction along the surface of the housing,
  the spectrometer performs calibration using the white reference surface when the shutter member is at the first position, and
  the spectrometer colorimetrically measures the measurement target when the shutter member is at the second position, and the aperture portion and the measurement target oppose each other.

2. The apparatus according to claim 1, wherein the shutter member is connected to the guide member.

3. The apparatus according to claim 1, wherein the shutter member is located outside the housing.

4. The apparatus according to claim 3, further including a press member configured to press the shutter member located at the first position toward the surface.

5. The apparatus according to claim 4, wherein the press member is configured to press the measurement target into contact with the surface when the measurement target covers the aperture portion and the shutter member is at the second position.

6. The apparatus according to claim 1, wherein the shutter member is located inside the housing.

7. The apparatus according to claim 1, further comprising a biasing spring configured to bias the shutter member from the second position toward the first position.

8. The apparatus according to claim 1, wherein the shutter member is configured to move between the first and second positions by rotating about an axis in a direction that is approximately parallel to the surface and orthogonal to the first direction.

9. The apparatus according to claim 8, further comprising a biasing spring configured to bias the shutter member in moving from the second position towards the first position.

10. The apparatus according to claim 9, wherein the biasing spring is configured to press the shutter member located at the first position towards to the surface.

11. The apparatus according to claim 1, wherein the shutter member is configured to move between the first and second positions by rotating about an axis that is approximately orthogonal to the surface.

12. The apparatus according to claim 1, wherein the guide member includes a cleaning member having an elastic body or a bristle-like brush,
  the housing includes a transparent cover that is configured to cover the aperture portion, and
  the cleaning member and the transparent cover are configured to slide when the guide member moves in the first direction.

13. The apparatus according to claim 1, wherein the surface of the shutter member that opposes the aperture portion or an end surface of a wall portion that surrounds the white reference surface comes into contact with a periphery of the aperture portion of the surface when the shutter member is at the first position.

14. The apparatus according to claim 1, wherein the housing includes a transparent cover that is configured to cover the aperture portion, and
   a shadow-casting region of the shutter member on the surface covers at least the entirety of the transparent cover when the shutter member is at the first position.

\* \* \* \* \*